(12) United States Patent
Romero Romero et al.

(10) Patent No.: US 11,369,514 B2
(45) Date of Patent: Jun. 28, 2022

(54) DEVICE AND METHOD FOR FRACTURING AND REMOVING OCULAR LENSES

(71) Applicant: Universidad de Los Andes, Bogota (CO)

(72) Inventors: Rafael Orlando Romero Romero, Bogota (CO); Fernando Ramirez Rodriguez, Bogota (CO); Alejandro Arciniegas Castilla, Bogota (CO); Andres Leonardo Gonzalez Mancera, Bogota (CO)

(73) Assignee: UNIVERSIDAD DE LOS ANDES, Bogota (CO)

( * ) Notice: Subject to any disclaimer, the term of this patent is extended or adjusted under 35 U.S.C. 154(b) by 525 days.

(21) Appl. No.: 16/368,025

(22) Filed: Mar. 28, 2019

(65) Prior Publication Data
US 2020/0306084 A1   Oct. 1, 2020

(51) Int. Cl.
*A61F 9/007*   (2006.01)

(52) U.S. Cl.
CPC ...... *A61F 9/00763* (2013.01); *A61F 9/00736* (2013.01); *A61B 2217/005* (2013.01); *A61B 2217/007* (2013.01)

(58) Field of Classification Search
CPC ............ A61F 9/00763; A61F 9/00736; A61B 2217/005; A61B 2217/007; A61B 2017/00685
See application file for complete search history.

(56) References Cited

U.S. PATENT DOCUMENTS

| | | |
|---|---|---|
| 3,976,077 A | 8/1976 | Kerfoot, Jr. |
| 3,996,935 A * | 12/1976 | Banko .............. A61B 17/32002 606/521 |
| 4,061,146 A | 12/1977 | Baehr et al. |
| 5,891,153 A * | 4/1999 | Peterson ............. A61F 9/00736 606/107 |
| 2016/0067089 A1 | 3/2016 | Sasazaki et al. |

FOREIGN PATENT DOCUMENTS

EP   0310285 A2   4/1989

OTHER PUBLICATIONS

Written Opinion for Corresponding International Application No. PCT/IB2020/052645 (19 Pages) (dated Aug. 20, 2020).

* cited by examiner

*Primary Examiner* — Tuan V Nguyen
*Assistant Examiner* — Rachel S Highland
(74) *Attorney, Agent, or Firm* — Lucas & Mercanti, LLP

(57) ABSTRACT

The present invention relates to a device for fracturing and removing ocular lenses. The device mainly comprises a rotational screw drill, a sleeve and a hydraulic suction system. The rotational screw drill has reversed conical propellers which help to grind the particles. The rotational screw drill is housed in a sleeve, which comprises a rigid cylinder and a suction cup. The suction cup has a bell or funnel shape with an elliptical cross-section. Finally, the hydraulic suction system is key for the present invention performance. Also, the invention relates to a method comprising the steps of breaking, splitting the cataract or lens tissue and simultaneously or subsequently grinding the particles inside the sleeve by means of the rotational screw drill and the sleeve, and finally removing them from the medium via the sleeve by means of a hydraulic suction system.

16 Claims, 16 Drawing Sheets

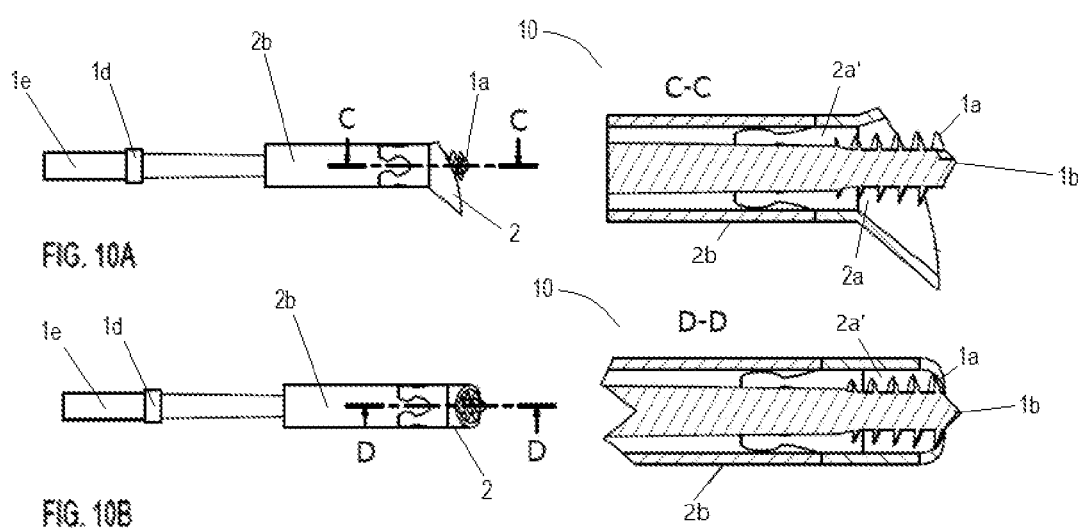

DEVICE AND METHOD FOR FRACTURING AND REMOVING OCULAR LENSES

FIELD OF THE INVENTION

The present invention relates to a surgical device for ophthalmic procedures and a method for fracturing and extracting ocular lenses material with or without cataracts.

BACKGROUND OF THE INVENTION

According to the World Health Organization (WHO), cataracts is the first cause of blindness in countries with low and medium income and it is the second one worldwide. A cataract is the progressive opacity and hardness of the ocular lenses caused by protein aggregation within the lens.

There are several techniques and devices well known in the prior art for cataracts surgical procedures, which can be used to remove the cataracts, and therefore, to reduce the problem of blindness associated therewith. All of the existing devices involve a hand piece, which supports a small tool being inserted in the eye through an incision, i.e. a small cut, made in the corneo-scleral limbus of the eye.

Extra Capsular Cataract Extraction (ECCE) and phacoemulsification are the primary methods for removing or extracting ocular lenses.

The extracapsular extraction procedure (ECCE) includes a corneal incision of about 6 to 8 mm long, which is larger than the cut made in phacoemulsification. The ECCE removes the cataract, mostly in one piece, by means of a combined suction and small tool work. Intra Ocular lenses (IOLs) are then implanted as a replacement of the eye's natural lens. ECCE is one of the most antique methods. It requires suture of the incision and a long period of recovery. The stitches may occasionally generate astigmatism.

In the phacoemulsification procedure, the ophthalmic surgeon uses a small tool which is introduced through a very small cut/incision in the corneo-scleral limbus of the eye. The phacoemulsificator produces ultrasonic movements of its tip to break up the cataracts tissues into small pieces. Subsequently, the suction system removes the particles and fragments through the small incision. Document U.S. Pat. No. 8,439,938 teaches that the phacoemulsification works by hitting the cataract with a needle at ultrasonic speed, wherein a hydraulic suction system drags free particles and removes them as soon as the cataract is being broken. The incision made is a 3 mm long cut in the corneo-scleral limbus of the eye.

In addition to the above, document U.S. Pat. No. 8,439,938 also teaches that the method involves cavitation and also releases a high amount of heat energy, which is why the phacoemulsificator needle requires to be manufactured with a special and expensive high resistance material. Moreover, the heat produced inside the anterior chamber of the eye may require a refrigeration system, which increases the costs of the device involved in this technique.

The advantage of phacoemulsification over extracapsular extraction procedure (ECCE) is that the incision in the eye is smaller, reducing thereby the risk of induced post-operative astigmatism. Nevertheless, ultrasonic systems used in phacoemulsification are expensive. Moreover, the technique requires a long training period for the surgeon in order to control the skills necessary to perform the procedure in a safe manner.

On the other hand, milling had been explored experimentally as an alternative technique to remove ocular lenses. For instance, patent JPH04231036 reports a hand tool for removing lenses. It comprises an elongated housing means including a driving motor; wherein said motor includes a rotatable chuck portion at its front edge, such as a head with a roughly rounded appearance, with curved teeth radially extending from the central portion of the drill. In this method, the cataract bulk is fully machined, removing tissues layer by layer of the contact surface. However, there are problems associated with this configuration, bearing in mind that there is an undesirable spreading of small pieces from the breaking of tissues, which are not properly isolated from the lens capsule of the eye.

The drilling technique has the advantage of increasing efficiency at breaking the cataract; however, this method is not a standard procedure in human beings due to the potential damage of the tissues inside the eye, predominantly the iris and endothelium, induced by the rotation of the cataract, dispersion of particles, and dynamic flows in the anterior chamber of the eye.

The present invention, however, solves those problems by means of a device (10) and a method comprising the steps of breaking, splitting a cataract or lens (100) tissue and simultaneously or subsequently, grinding particles inside a sleeve (2) through a rotational screw drill (1) and a sleeve (2), and finally removing them from the medium through the sleeve (2) by means of a suction system (9). These are useful in intraocular surgery, particularly, in cataract or lens removal surgery. The device (10) comprises a rotational screw (1) with a special tip configuration for manipulating cataracts and other tissues that have to be removed from the anterior chamber of eye (101). The special tip configuration consists of an Archimedes screw, which along with the suction system (9), avoids the undesirable spreading of pieces of the lens and direct them towards the sleeve (2), where a grinding area is formed between the Archimedes screw arrangement and the sleeve (2).

SUMMARY OF THE INVENTION

The present invention relates to a device (10) for fracturing and removing ocular lenses. The device mainly comprises a rotational screw drill (1), a sleeve (2) and a hydraulic suction system (9). The rotational screw drill (1) has a neck (1d), a top lock (1c), a tip edge (1b), and a screw edge (1a). The rotational screw drill (1) is housed in a sleeve (2), which comprises a rigid cylinder (2b) and a suction cup (2a). The suction cup (2a) has a bell or funnel shape with an elliptical cross-section. Finally, the hydraulic suction system (9) is key for the present invention performance.

Secondly, the invention provides a method for fracturing and removing lenses, specifically, by inserting the sleeve (2) through a 12 meridian incision in the corneo-scleral limbus, which is 3.00 to 3.5 mm long; irrigating the anterior chamber (101); capturing or fixing the lens (100) to the suction cup (2a) by activating the suction system (9) through the sleeve (2); irrigating and dragging the anterior chamber (101) in a synchronized manner between the suction and irrigation systems. Finally, the main difference with traditional methods is based on fracturing the lens or cataract by drilling the entire lens with the rotational screw (1); breaking the surface and the inner part of the lens (100) in pieces of a suitable size; simultaneously or subsequently vacuuming the lens particles, and removing the device (10) from the eye.

BRIEF DESCRIPTION OF THE DRAWINGS

FIGS. 10A and 10B are, respectively, side and top views of the device (10) with the corresponding enlarged and cross-section views according to the present invention;

DESCRIPTION OF THE PREFERRED EMBODIMENTS

Figure 1:
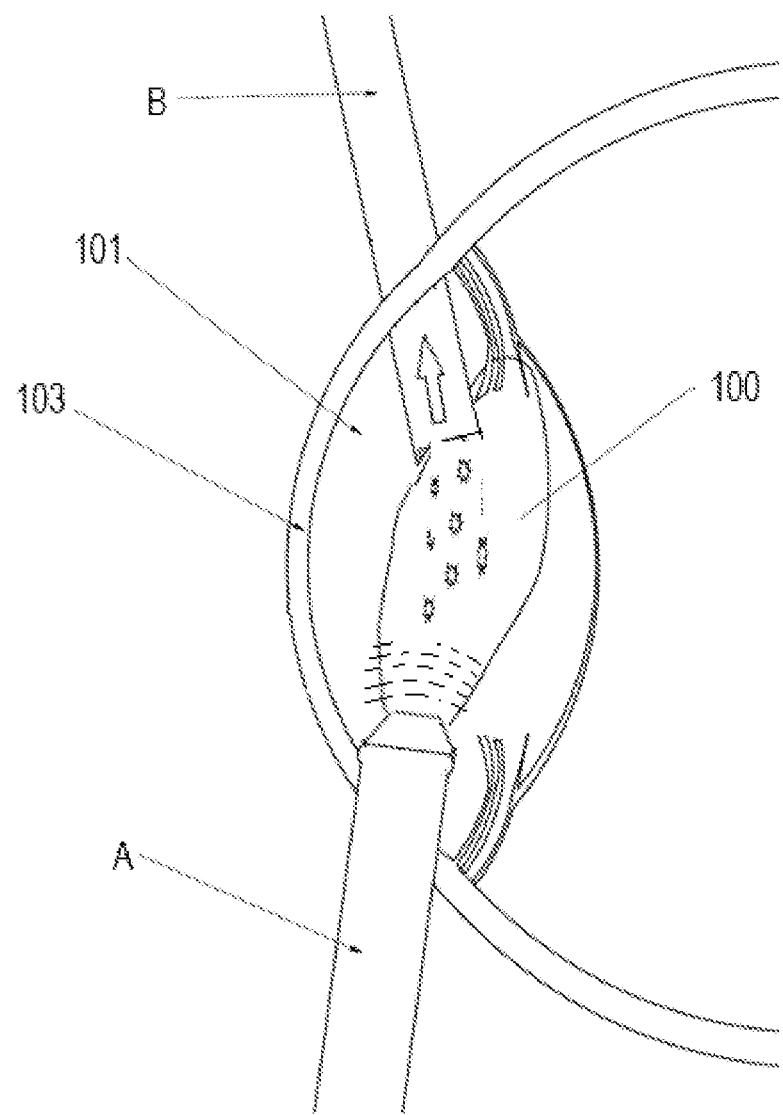
FIG. 1 is a schematic, side view, cross-section illustration of a human eye's anterior chamber (101) during cataract surgery in accordance with the prior art.

The present invention aims to provide an improved, low cost device (10) and a method for fracturing and removing ocular lenses. The device (10) and method break the ocular lens (100) by using a rotational screw drill (1) covered by a sleeve (2). The system fractures the lens (100) or cataract tissues in particles to a suitable size and then, said particles are extracted and isolated from the medium by using a hydraulic suction system (9). The rotational screw drill (1) generates scission to the ocular lens (100) and reduces the particles by grinding them (in case of existence of particles larger than the suitable size) inside a suction cup (2) while pressing the particles with the screw against the inner walls of the sleeve (2). Once the particles have a suitable size, these are extracted from the eye by means of the suction system. The incision size to introduce the suction cup (2a) into the eye's anterior chamber (101) is small enough (in the range of 3.0 to 3.5 mm) to avoid residual astigmatism.

According to the present invention, the rotational screw drill (1) has two or more reversed conical propellers (1f). These propellers make scission on the ocular lens by digging inside the lens/cataract for breaking it. To pick up the pieces of lens/cataract dispersed in the medium, the sleeve (2), which is connected to the hydraulic suction system (9), captures them. At the same time, the reversed conical propellers (1f) help to grind the particles produced by the first breaking, reducing their size inside the sleeve (2). This avoids the undesirable particles dispersion in the medium of the anterior chamber (101) of the eye. Further to this advantage, the use of the rotational screw drill (1) has a low energy consumption considering that it does not require high movement frequencies. Other advantage is that the transport and grinding of the particles by means of the reversed conical propellers (1f) ease the capture of particles while the screw drill edge (1b) is fracturing/breaking the lens or cataract. Moreover, the device (10) and method of the present invention have a negligible temperature increase.

In relation to the reversed conical propellers (1f) of the rotational screw drill (1), the advantages of having two or more propellers are: the vibrations of the device to avoid the risk of damaging any eye healthy tissues including endothelium and iris are reduced, and the volume of the lens scissioned and removed by rotation of the screw is increased. Although it would be desirable to have a higher number of propellers, the number of propellers is limited by manufacturing conditions.

In an embodiment of the present invention, the rotational screw (1) passes through the sleeve (2) and the suction cup (2a).

In another embodiment of the present invention, the sleeve (2) comprises a rigid cylinder (2b) and a suction cup (2a). The designed suction cup (2a) is an extension of the rigid cylinder (2b), and it has a funnel or "bell" shape with an elliptical cross-section. The suction cup (2a) must be flexible in order to fit through the small incision made to the eye in the procedure. Moreover, the rigid cylinder (2b) must avoid looseness, allowing the introduction of the suction cup (2a) inside the anterior chamber (101) of the eye.

In addition to the aforementioned advantages, the suction cup (2a) according to the present invention helps to avoid damage to the eye since the suction cup (2a) isolates the eye from temperature, particle dispersion, and flow shear forces.

Further, in accordance with a preferred embodiment of the present invention, the rigid cylinder (2b) provides a lifting pressure that provides support to the rotational screw (1) easing its control from outside the chamber (4a).

Still further, according to a preferred embodiment of the invention, the hydraulic suction system (9) extracts the particles with a maximum size limit. Particles produced by the grinding or drilling area (2a'), which is formed by the reversed conical propellers (1f) and the inner surface of suction cup (2a), are pulled towards the inner parts of the suction cup (2a) and sleeve (2) by the hydraulic suction system (9).

Still further, in accordance with another preferred embodiment of the present invention, the reversed conical propellers (1f) have a screw drill edge (1a) with a positive attack angle, which allows the splitting, breaking, and the subsequent dragging of particles inside the rigid cylinder (2b) in order to be removed from the device (10).

Yet further, according to another preferred embodiment of the invention, the diameter of the reversed conical propellers (1f) is smaller than the incision size required in the corneoscleral limbus of the eye and the inner diameter of the sleeve (2).

In addition to the above, in another preferred embodiment of the invention, the length of the rotational screw drill (1) forming the grinding area (2a') along with the rigid cylinder (2b) and the suction cup (2a), may be in the range between 2 and 6 mm beyond the suction cup (2a), preferably between 3 and 5 mm.

In addition, according to another embodiment of the present invention, the diameter of the reversed conical propellers (1f) increases along the rotation axis of the rotational screw drill (1) towards the screw drill edge (1a). It has a cutting angle between 5° and 45° relative to the rotation axis, preferably between 5° and 15° in order to generate the splitting, breaking, or scission of the lens, thereby pulling the particles backwards for their subsequent grinding.

Still further, in another embodiment of the present invention, the screw drill tip (1b) may have a positive (5° to 45°) or neutral (0° to 5°) cutting angle, which allows centering of the drilling direction and aligning the rotational screw drill (1).

In another further embodiment of the invention, the suction cup (2a) also helps to support the lens (100) and particles for fracturing them with the reversed conical propellers (1f).

In another further embodiment of the invention, the suction cup (2a) is foldable in order to be introduced into the anterior chamber (101) of the eye; once inside, it recovers its shape (on a complete elastic process) to be able to capture and support the cataract.

In another further embodiment of the invention, the rigid cylinder (2b) is a thin walled tube that guides the rotational screw drill (1) and avoids the contact of the reversed conical propellers (1f) with the ocular tissues.

For the method of the present invention, an improved device (10) comprising a rotational screw (1) and a sleeve (2) is used for breaking, splitting, fracturing, grinding, removing, and extracting pieces of cataract or lens (100) tissues easily. Essentially, the method of the present invention comprises the steps of breaking, splitting the cataract or lens (100) tissue and simultaneously or subsequently, grinding the particles inside the sleeve (2) by means of the rotational screw drill (1) and the sleeve (2), and finally removing them from the medium through the sleeve (2) by means of a hydraulic suction system (9).

With this arrangement, the physician is able to introduce the system through an incision made in the corneo-scleral limbus of the eye, fix the cataract or lens (100) tissue to the suction cup (2a), and drill the cataract with the rotational screw (1), which could be moved retractably back and forward along the longitudinal axis of the sleeve (2).

The standard method for the extraction of ocular lens, regardless of the device employed for the surgery, includes the following steps:
 a. Making a first paracentesis in the cornea (103) for inserting a viscoelastic fluid, for example, sodium hyaluronate;
 b. Injecting a viscoelastic fluid for increasing the volume of the anterior chamber (101) to perform the lens extraction;
 c. Making a circular cut (5 to 6 mm diameter) on the anterior capsule of the lens and separating the ocular lens (100); this process is known as capsulorhexis;
 d. Inserting a fluid between the ocular lens (100) and the capsule lens (Hydrodissection);
 e. Making a second paracentesis in the cornea (103) at 12 meridian, for inserting the lens breaking tool;
 f. Fragmenting and removing the ocular lens (100); and
 g. Inserting a lens replacement (Intra Ocular Lens—IOL).

According to the present disclosure, the device (10) of the invention is used to carry out step f of the method as mentioned above.

In another embodiment of the present invention, step f) of fragmenting and removing the ocular lens (100), comprises the following sub-steps:
 i. Irrigating the anterior chamber (101);
 ii. Inserting the sleeve (2) through the 12 meridian incision (second paracentesis);
 iii. Capturing or fixing the lens (100) to the suction cup (2a) by activating the hydraulic suction system (9) through the sleeve (2);
 iv. Irrigating the anterior chamber (101) in a synchronized manner between the hydraulic suction system (9) and irrigation system (30);
 v. Fracturing the lens or cataract by drilling the surface of the lens with the rotational screw drill (1) which rotates at angular speed between 100 and 1200 rpm;
 vi. Breaking the surface and the inner part of the lens (100) in pieces of a suitable size;
 vii. Simultaneously or subsequently vacuuming the lens particles; and
 viii. Removing the device (10) from the eye.

In step a), the incision has a maximum length of 3.5 mm, preferably between 1.0 and 3.5 mm, in order to avoid side effects such as astigmatism, infections, and tissue damage. Further, to allow the insertion of the sleeve (2), the suction cup (2a) is temporally folded or collapsed.

In sub-step ii., the insertion and activation of the irrigation system (30) avoids the collapse of the anterior chamber (101) while performing the fracturing and the extraction of the lens (100). In a preferred embodiment of the invention, the hydraulic suction system (9) synchronizes the irrigation-aspiration processes inside the anterior chamber (101) of the eye.

In sub-step iii., the activation of the suction system (9) eases the capture of the ocular lens (100), and the inner part of the sleeve (2) conducts the flux to a waste deposit through the device (10).

In sub-step iv., the irrigation (30) and hydraulic suction system (9) work simultaneously in order to maintain the volume of the anterior chamber (101).

In sub-step v. the screw drill edge (la) performs the drilling of the ocular lens (100). The fracturing of the ocular lens (100) is carried out through the reversed conical propellers (1f), starting from the screw drill edge (la) to obtain lens particles.

Moreover, in sub-step v, the grinding of the lens particles occurs in the grinding area (2a') formed by the reversed conical propellers (1f) and the suction cup (2a) where the particles are trapped and grinded until they have a suitable size to be extracted through the rigid cylinder (2b).

In some preferred embodiments of the present invention, the device (10) is preferably used with an irrigation instrument tip (30'), which helps to fix/push the lens or cataract against the device (10), namely against the suction cup (2a) while the rotational screw drill (1) penetrates the surface and breaks up the lens or cataract. In another embodiment, the irrigation system (30) may be incorporated in the device (10) in order to reduce the invasiveness in the eye. In this case, the irrigation system (30) and hydraulic suction system (9) operate in an interleaved manner.

In another preferred embodiment of the invention, the device (10) is attached to a hand-piece (20).

In another preferred embodiments of the present invention, the device (10) has the irrigation system (30) and the hydraulic suction system (9) incorporated therein, together with the irrigation instrument (30') which could be a stick or rod of any surgically acceptable material. In these embodiments of the invention, the control system (80) electronically controls the irrigation system (30) and hydraulic suction system (9).

In another preferred embodiment of the invention, the device (10) is directly and mechanically connected to probes of any suitable length, which provide the power, the irrigation of the balanced salt solution, i.e., a balanced saline solution, and the suction of fluids from the eye by means of a hydraulic suction system, wherein all of these are controlled by a suitable control system (80).

The novel and inventive features of the present invention, its structure, and its operation will be best understood from the accompanying description and the attached figures.

In order to get a better understanding, each component of the device has a designated reference number throughout the various figures. Reference is now made to FIG. 1 which schematically illustrates a cross-section side view of the human eye's anterior chamber with the lens (100), which is split by means of an instrument (A), in this case, an ultrasonic tool. After the breaking of the lens (100), the suction system and the surgical instrument manipulate fragments and particles. The surgeon introduces the instrument (A), into the anterior chamber (101) of the eye, through a small incision. In some cases, the surgeon introduces another extraction tool (not shown) into the anterior chamber of the eye (101), through a second smaller incision.

Figure 2:
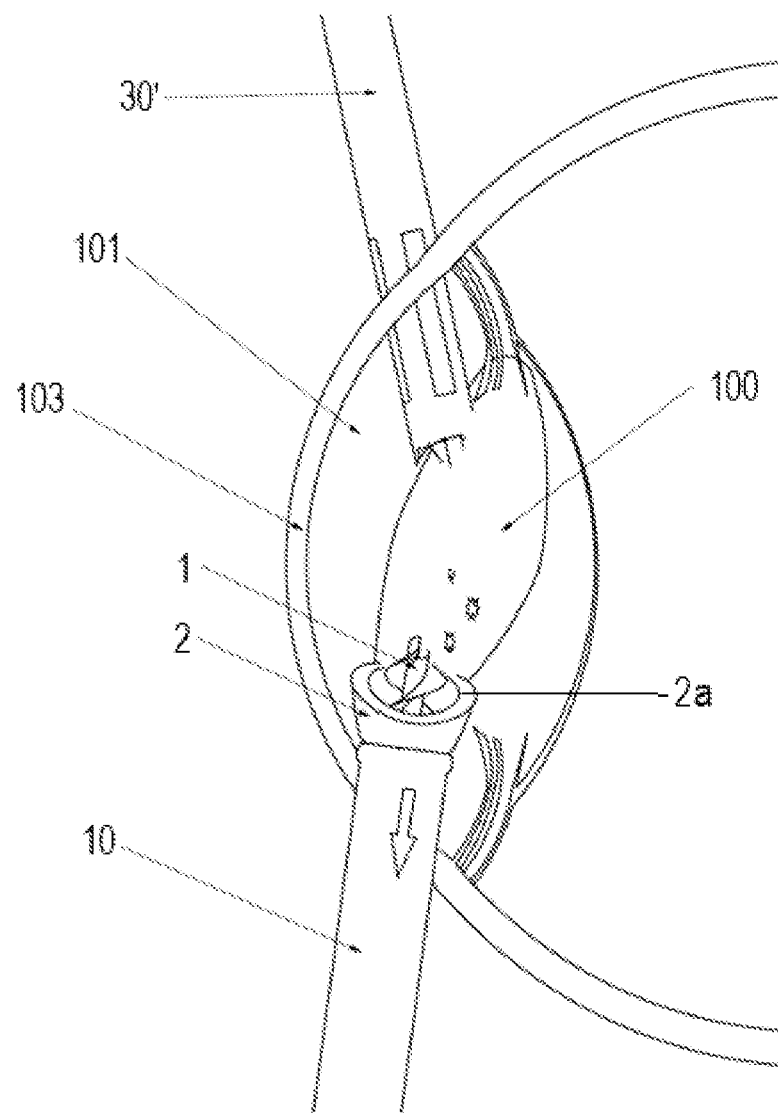
FIG. 2 is a schematic, side view, cross-section illustration of a human eye's anterior chamber (101) during cataract surgery using the device (10) of the present invention.
Figure 13:
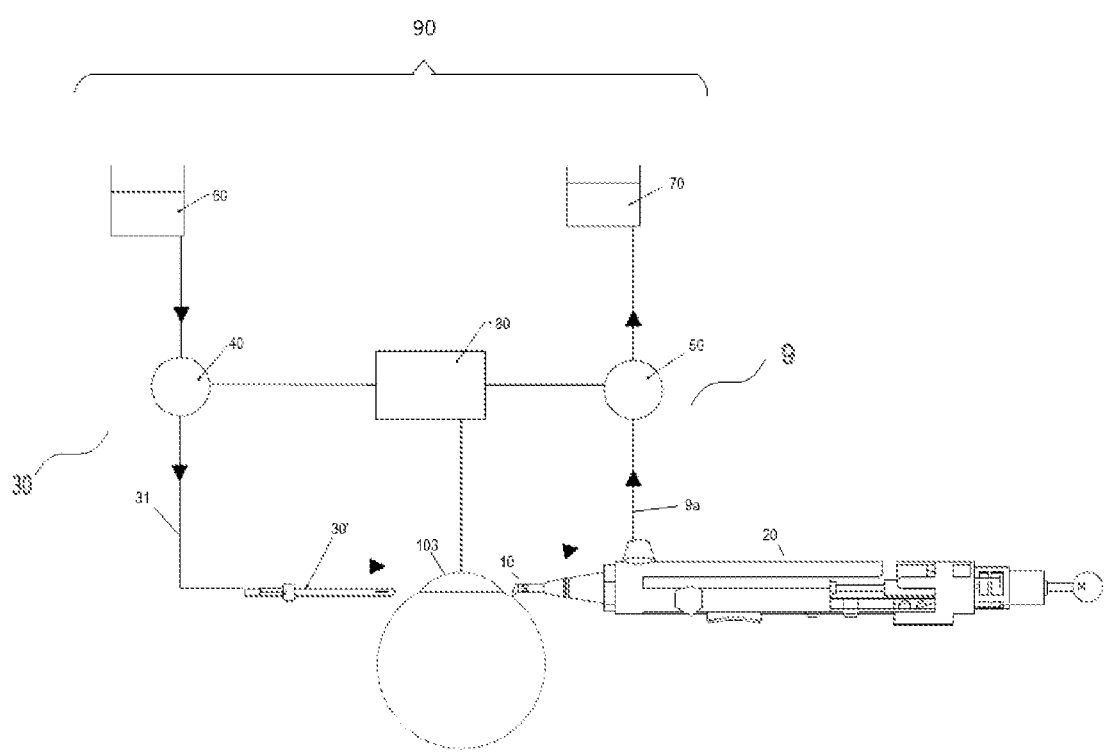
FIG. 13 shows the hydraulic system (90) which comprises control system (80), reservoir (60), waste deposit (70), suction pump (50), pump (40). This figure also illustrates the configuration of the entire system around the eye.

FIG. 2 is a schematic illustration related to a cross-section side view of human eye's anterior chamber wherein the surgeon introduces the device (10) of the invention through a corneo-scleral incision. The sleeve (2) supports the lens (100) via the vacuum created inside the device (10) by the action of the hydraulic suction system (9) (FIG. 13). When the lens (100) is held by the suction cup (2a) (FIG. 3A), the rotational screw drill (1) breaks the lens (100) by activating the rotation. The irrigation instrument tip (30') may push and fix the lens (100) along with the suction cup (2a) to help the device (10) penetrate the lens (100) so the rotation of the cataract or lens is prevented.

Figure 3:
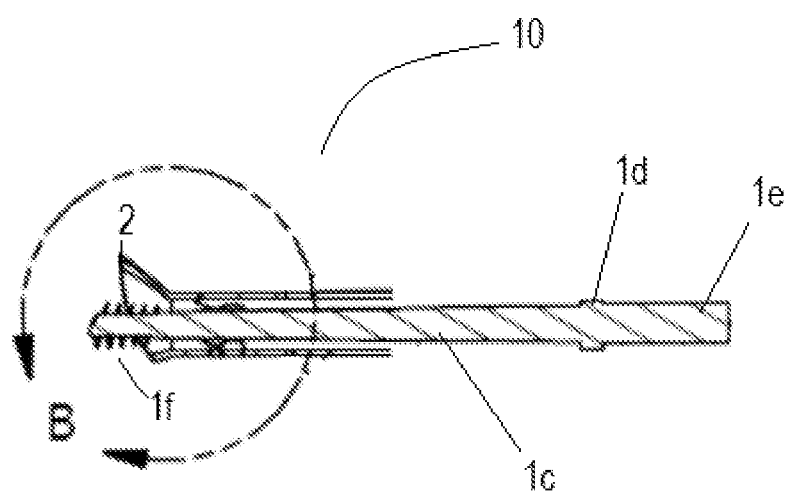
FIG. 3 and FIG. 3A are schematic and enlarged, side view illustrations of the device (10) according to the present invention.
Figure 3A:
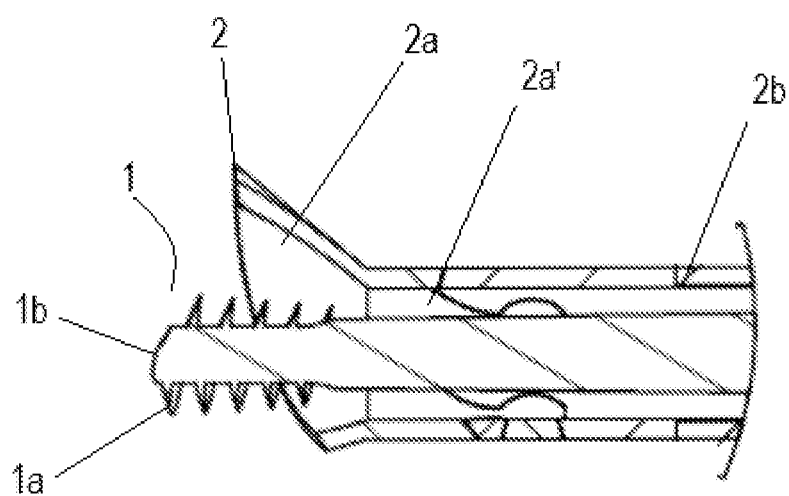
Figure 5:
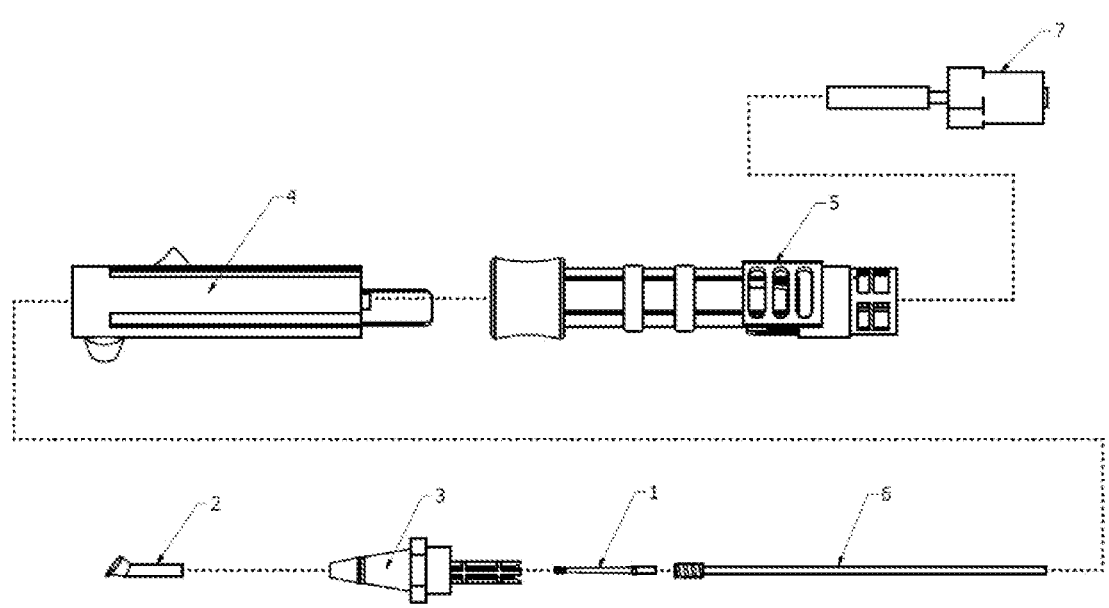
FIG. 5 is an exploded view of the hand-piece or tool (20) comprising the device (10) according to the present invention.

In relation to FIG. 3, it is a schematic illustration related to the arrangement of the device (10); wherein the rotational screw drill (1) may have variable length and it comprises a base (1e) which is the part where the rotational screw drill (1) may be attached to the hand-piece (20), as shown in FIG. 5; a neck (1c), a top lock (1d), a tip edge (1b), a screw edge (1a), and reversed conical propellers (1f) (FIG. 3A). The rotational screw drill (1) is housed in a sleeve (2), which comprises a rigid cylinder (2b) and a suction cup (2a) (FIG. 3A), wherein the suction cup (2a) has a funnel or "bell" shape with an elliptical cross-section.

Figure 4:
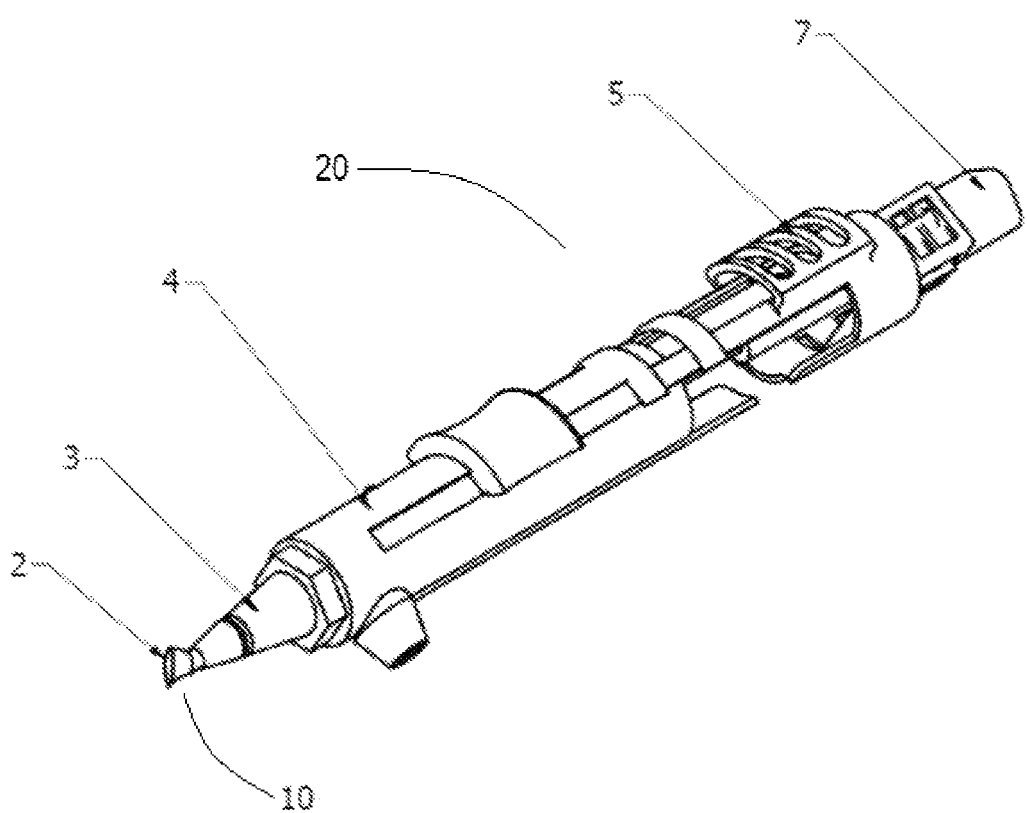
FIG. 4 is a schematic perspective view of the hand-piece or tool (20) comprising the device (10) according to an embodiment of the present invention.

With respect to FIG. 4, this figure shows the hand-piece (20) where the device (10) is mechanically adjusted. The hand-piece (20) includes the device (10) for fracturing and removing ocular lenses, and also includes a lid (3), a chassis (4), a plunger mechanism (5), an extender shaft (6) (FIG. 5), and a motor (7).

FIG. 5 shows the configuration of the hand-piece (20). The lid (3) has a cavity (3b) (FIG. 6A) and an approximation neck (3c) that allows transmitting the suction through the sleeve (2) while supporting its alignment along the rotation axis.

Figure 6A:
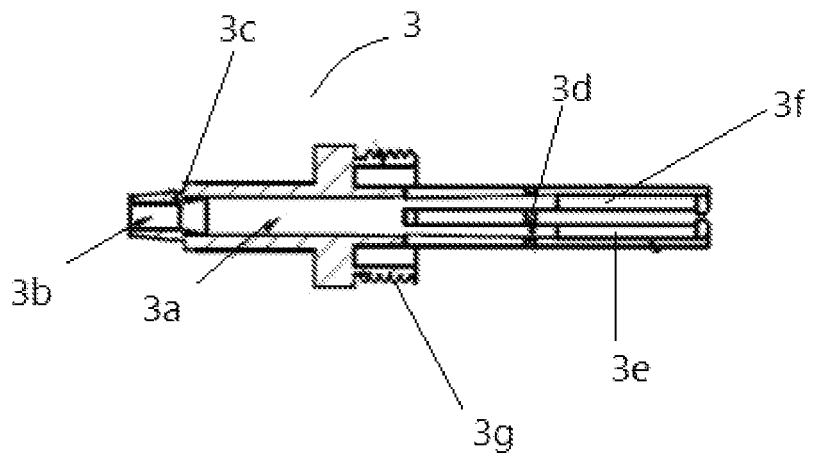
FIGS. 6A, 6B and 6C are, respectively, cross-section view, lateral view, and perspective view of the lid (3) according to the present invention.
Figure 6B:
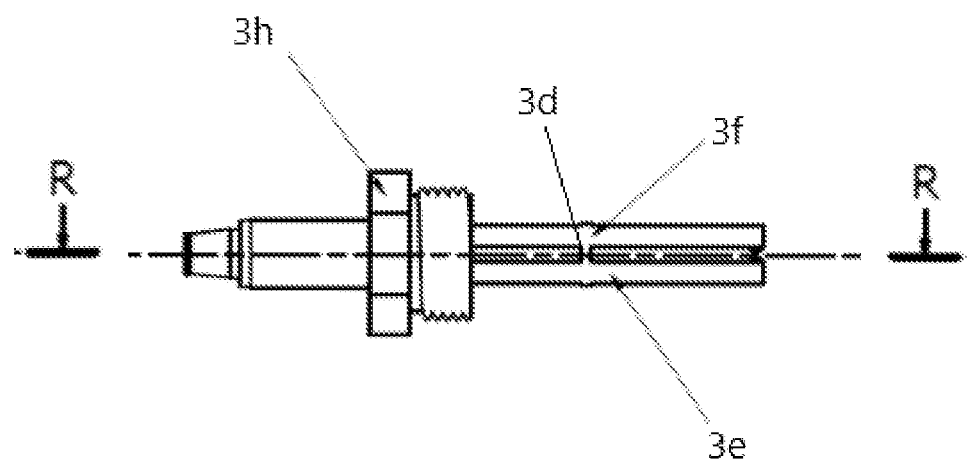
Figure 6C:
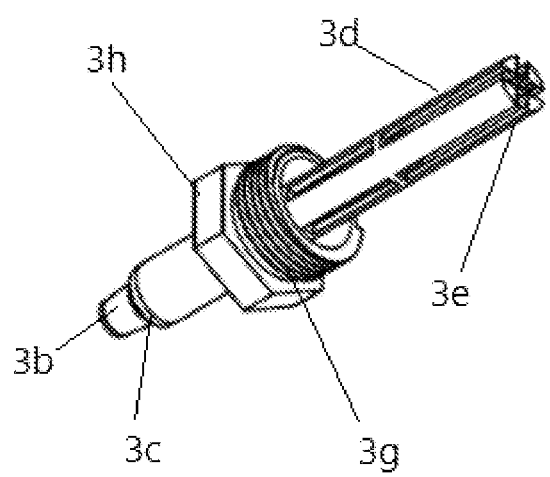

Referring to FIGS. 6A-6C, these correspond to a side view, a perspective view, and a cross-section view of the threaded lid (3) detailed in FIG. 5, respectively. The threaded lid (3) includes a hollow conic section (3a), a hexagonal base (3h), a threaded connector (3g), multiples longitudinal blades (3e), a funnel (3a), and a stiffening ring (3d). The funnel (3a) is a cavity with varying diameters along the length of the funnel (3a) and (3c). At the distal end of the funnel (3a), there is a smaller cavity (3b), which rigidly supports the sleeve (2) minimizing vibration of the extender shaft (6) and allowing the fragmented particles to pass therethrough.

Figure 7A:
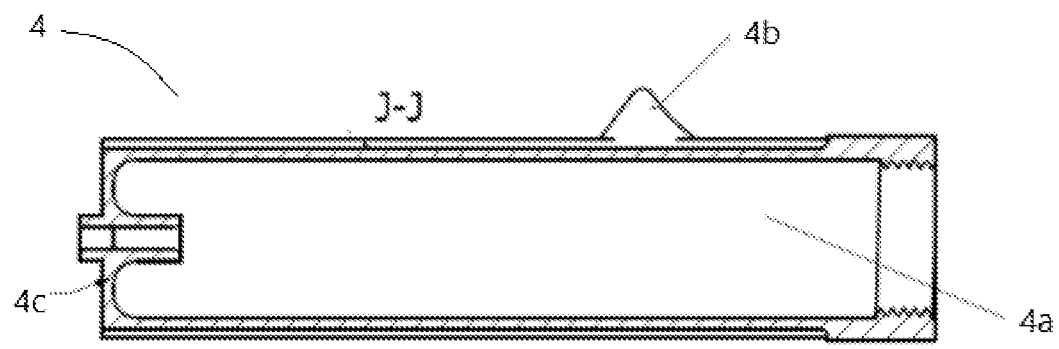
FIGS. 7A, 7B and 7C are, respectively, bottom view, side view, and front cross-section view taken along lines K-K of the chassis (4) according to the present invention.
Figure 7B:
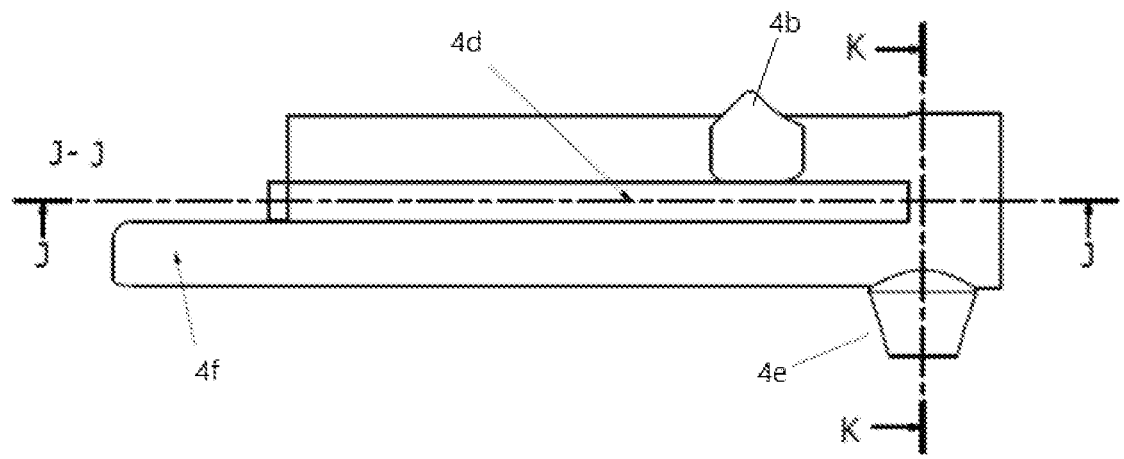
Figure 7C:
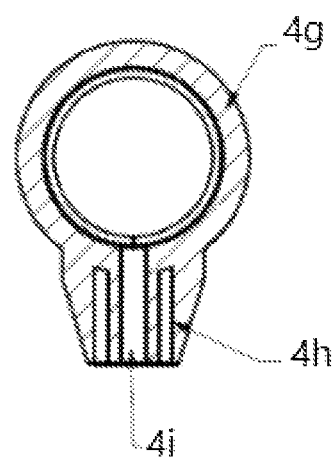

The chassis (4) of the hand-piece (20) shown in FIG. 4 is detailed in FIGS. 7A, 7B and 7C. The chassis is the structure that provides the grabbing area for manipulating the device (10) while fracturing and removing the ocular lens (100), and also provides rigid support to the other components of the device (10). In addition, the chassis (4) is the main cylinder, which contains a vacuum chamber (4a) (FIG. 7a). The exterior structure of the chassis (4) also comprises an index finger support (4b), a middle finger support (4e), a main cylinder back (4c), and sliding rails (4d). The middle finger support (4e) also has a conical trunk shape with a special inner configuration and comprises a hose connector (4h) for connecting the probe (9a) of the hydraulic suction system (9), a thicker threaded wall (4g), and a middle cavity (4i), as shown in FIG. 7C. The chassis (4) is a hollow cylinder that supports the lid (3), the extender shaft (6), and the plunger mechanism (5). The index finger support (4b) is a triangle-shaped part which does not move relative to the chassis (4). The conical trunk (4e) also allows connecting the suction probe (9a). The side blade (4f) is an extension of the main body (4). The cylinder back (4c) supports the extended shaft (6) and may include a bushing (not shown) to reduce the vibrations caused by the rotation of the shaft (6). The sliding rails (4d) are the guides for the plunger blades (5b and 5d).

Figure 8A:
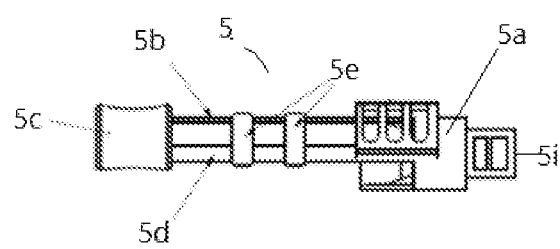
FIGS. 8A and 8B are, respectively, top view and side view of the plunger mechanism (5) according to the present invention.
Figure 8B:
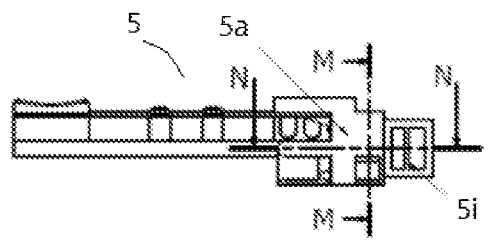
Figure 8D:
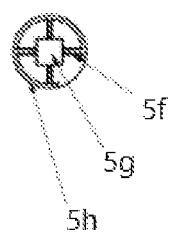
FIGS. 8C and 8D are, respectively, side and front views of the plunger mechanism (5) taken along lines N-N and M-M, respectively.
Figure 8C:
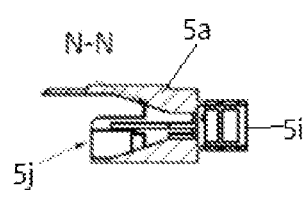
Figure 8E:
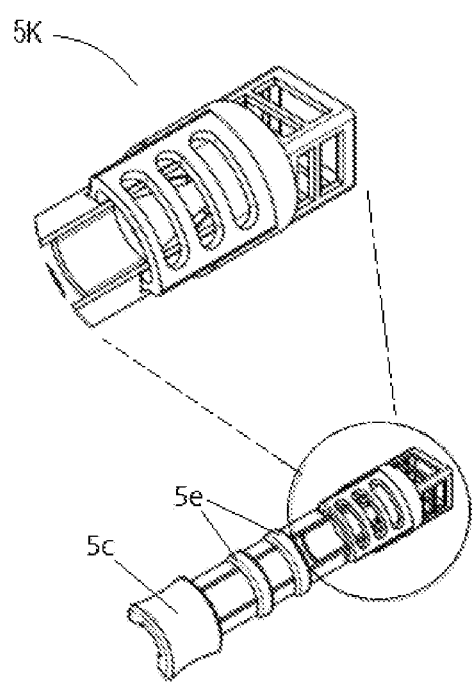
FIG. 8E is an enlarged perspective view of part 5K which may be comprised by elements 5a and 5i of the plunger mechanism (5)

The plunger mechanism (5) of the hand-piece (20) as shown in FIGS. 8A through 8E allows the control of the longitudinal displacement of the rotational screw drill (1) along the rotation axis. This part of the hand-piece (20) comprises a main body (5a), longitudinally blades (5b and 5d), a thumb actuator (5c), two stiffening rings (5e), and a motor basket (5i) as shown in FIG. 8A. The plunger mechanism (5) in its inner part comprises, as shown in FIGS. 8C and 8D, a support (5j) for the side blades (FIG. 8C), a stiffening cross (5f), a shaft hole (5g), and the main body wall (5h). FIG. 8E shows the basket for the motor (5i) and the main body (5a). The latter forms the anti-deflection shield (5k), which provides further strength and stability to the hand-piece (20). One of the functions of the plunger mechanism (5) is to provide further support to the handle piece (20). This part is designed according to the selected motor (7) and the chamber shape (4a). Its long and slim blades (5b and 5d) fit into the sliding rails (4d); it also provides support for the motor (7) weight. This design has also the purpose to fit the surgeon hand, specially the thumb and index supports. The design also makes easy to displace the plunger (5) along the sliding rails (4d).

Figure 9A:
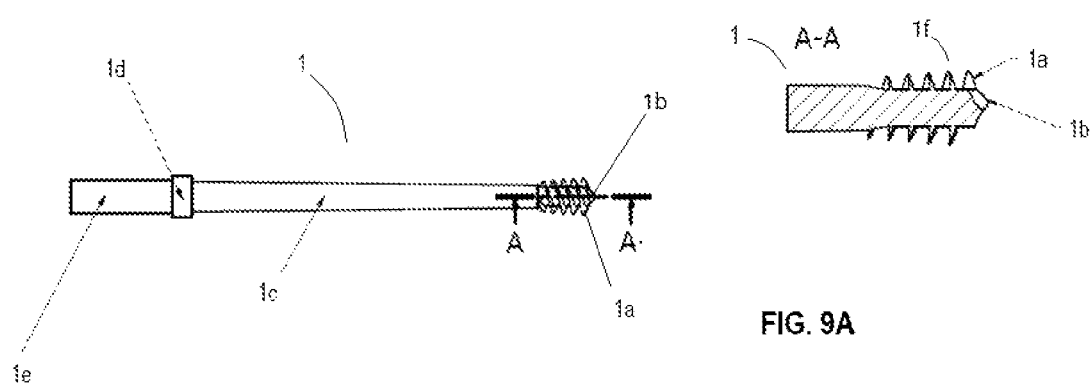
FIGS. 9A and 9B are, respectively, side and perspective view of the rotational screw (1) with the corresponding enlarged views, according to the present invention.
Figure 9B:
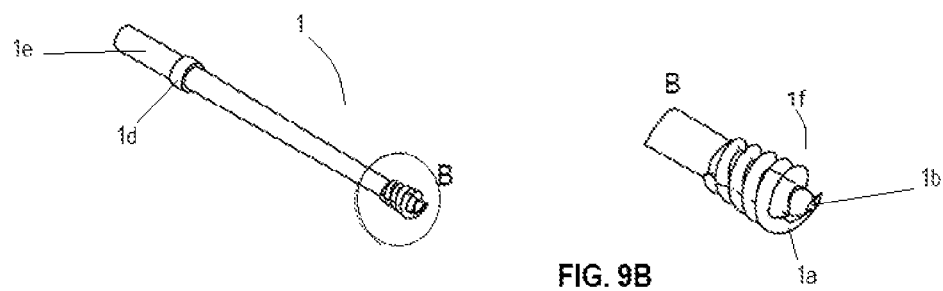

In relation to FIGS. 9A and 9B, these show the configuration of the rotational screw (1) which comprises a screw edge (la), a tip edge (1b), a top lock (1d), a base (1e), a neck (1c), and the Archimedes screw (1f), also referred to as reverse conical propellers (1f). As it can be seen in cross-section A-A, the Archimedes screw (1f) in FIG. 9A has a configuration wherein the height of each propeller is increased toward the tip edge (1b) in order to improve the extraction of lens' pieces (100) when the rotational screw (1) is activated through the sleeve (2) by means of the motor (7).

The base (1e) may be cylindrical and it couples with the shaft hole (6b) shown in FIG. 11. The Top Lock (1d) is a short cylinder or disc with a diameter larger than the base part (1e), for example, 1 or 2 mm more. The neck (1c) has a cylindrical shape with decreasing diameter towards the screw tip edge (1b). Finally, the rotational screw drill (1) has a twin reversed conical propeller (1f) (reversed because its diameter increases along its length to the tip edge (1b)). The base (1e) allows connecting the extender shaft (6) with the rotational screw (1); the neck (1c) fits into the vacuum chamber lid (3) and into the sleeve (2). The rotational screw (1) on the tip edge (1b) will be in direct contact with the lens (100). Moreover, the base (1e) allows the transmission of the rotation from the extender shaft (6) to the rotational screw (1), while the top lock (1d) on the top indicates if both parts, the rotational screw and the shaft, are well hooked on. The long neck (1c) produces hydraulic lift while rotating inside the threaded lid, which minimizes vibrations and increases accuracy. The designed shape of the screw (1) allows the fracture of the cataract to the suitable fragments sizes, and also to transport them along and around the screw (1) into the vacuum chamber (4a) through the suction cup (2a) and the rigid cylinder (2b) of the sleeve (2).

In connection with FIGS. 9A and 9B described above, FIGS. 10A and 10B show the cross-section C-C and D-D corresponding to the side and top views of the device (10). These also show the grinding area (2a') and the suction cup (2a).

Figure 11A:
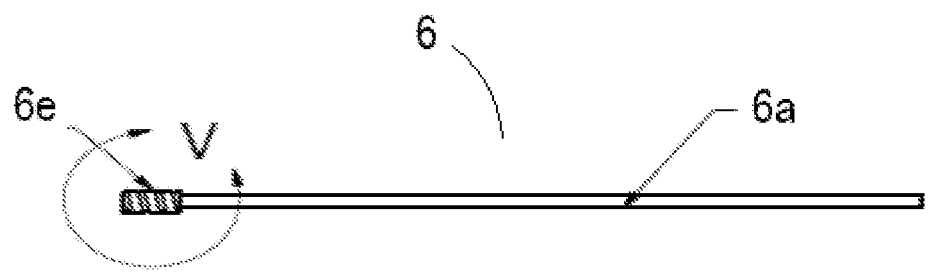
FIGS. 11A and 11B are, respectively, a side view and an enlarged cross-section of the extender shaft (6).
Figure 11B:
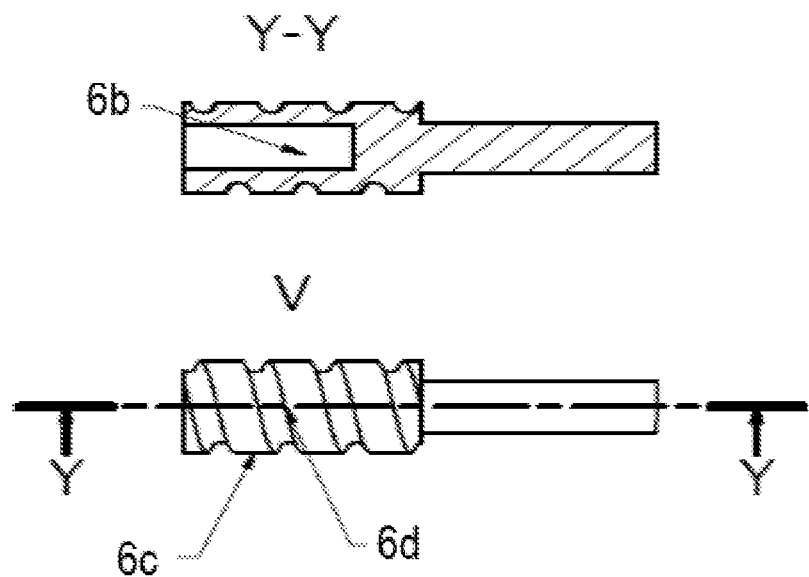

FIGS. 11A and 11B illustrate the extender shaft (6) which is the element for transmitting the torque from the motor (7) to the rotational screw (1) of the device (10), generating a rigid connection and minimizing the potential vibrations of the device (10). The motor (7) provides the necessary torque to operate the device (10). It also produces the least possible vibration with low energy consumption. The motor (7) can be powered by direct current or attached batteries.

Figure 12:
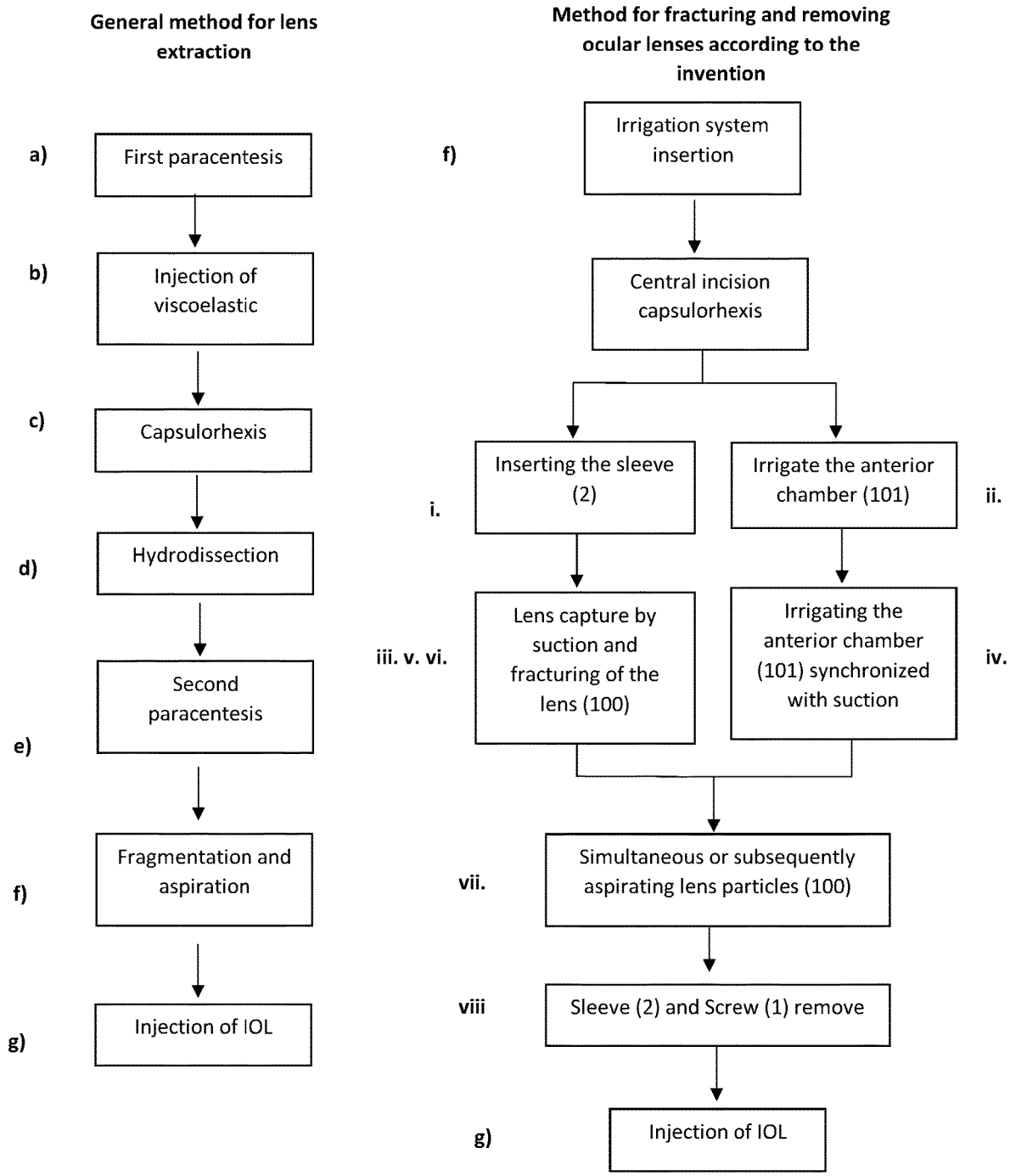
FIG. 12 shows the conventional method and the method implemented with the improved device (10).

FIG. 12 shows the general method for lens extraction which comprises the following steps:
   a. Making a first paracentesis at the cornea (103) for injecting a viscoelastic fluid;
   b. Injecting a viscoelastic fluid for increasing the volume of the anterior chamber of the eye (101) for performing the lens extraction;
   c. Separating the ocular lens (100) by means of a circular cut of the anterior capsule, 5 to 6 mm diameter, process known as capsulorhexis;
   d. Injecting a fluid between the ocular lens (101) and the capsule lens. (Hydrodissection);
   e. Making a second paracentesis in corneo-scleral limbus (103) at 12 meridian for inserting the lens breaking tool;
   f. Fragmenting and removing the ocular lens (100); and
   g. Injecting a lens replacement (Intra Ocular Lens—IOL).
   Step f. of fragmenting and removing the ocular lens (100), comprises the following sub-steps when using the present device:
      i. Irrigating the anterior chamber (101) by inserting the irrigation instrument tip (30');
      ii. Inserting the sleeve (2) through the 12 meridian incision (second incision);
      iii. Capturing or fixing the lens (100) to the suction cup (2a) by activating the hydraulic suction system (9) through the sleeve (2);
      iv. Irrigating the anterior chamber (101) in a synchronized manner between the hydraulic suction system (9) and the irrigation system (30);
      v. Fracturing the lens or cataract by drilling the surface of the lens with the rotational screw drill (1), which rotates at an angular speed between 100 and 1200 rpm;
      vi. Breaking the surface and the inner part of the lens (100) in pieces with a suitable size;
      vii. Simultaneously or subsequently vacuuming the lens particles; and
      vii. Removing the device (10) from the eye.

Finally, referring to FIG. 13, it shows a possible arrangement for the hydraulic system (90) according to the present invention. The irrigation system (30) and the hand-piece (20) bearing the device (10) are both connected respectively to pumps (40) and (50). The mechanical and electronic control system (80) drives the pumps via sensors that measure the height of the cornea (103) of the eye. The hydraulic system (90) also comprises a reservoir (60), which contains balanced salt solution to be injected in the eye. This reservoir (60) may have sensors and additional devices for controlling the temperature and the sterile conditions of the liquid. As it can be seen in FIG. 13, the pump (40) pumps the balanced salt solution from the reservoir (60) through a probe (31) towards the irrigation instrument tip (30') to the anterior chamber (101) of the eye, wherein the volume has to be maintained. The suction system (90) drags the particles and part of the liquid in the anterior chamber (101) of the eye through the device (10) toward the waste recipient (70) through the probe (9a).

This invention has been described with a limited number of embodiments, it will be appreciated that many variations and/or modifications of the present invention may be made.

It will be appreciated by those skilled in the art, that the present invention is not limited to the preferred embodiments of the invention defined herein and that no limitations are intended to the details of the construction or design shown herein other than as defined in the appended claims:

We claim:

1. A device for scissioning, grinding and removing ocular lenses, wherein said device comprises:
   a rotational screw drill (1) comprising a neck (1c), a screw edge (1a) and a screw tip edge (1b), the screw edge (1a) comprises reversed conical propellers (1f), wherein an external diameter of the reversed conical propellers (1f) increases towards the screw tip edge (1b) and wherein the screw tip edge (1b) has a positive cutting angle relative to the rotation axis of the rotational screw drill, and a positive attack angle with respect to the lens;
   a sleeve (2) housing the rotation screw drill (1), the sleeve comprising a flexible and elastic suction cup (2a) and a rigid cylinder (2b), wherein the suction cup has a bell or funnel shape with an elliptical cross-section and the rigid cylinder comprises a drilling area (2a');
   a lid connected to the sleeve for retraining the sleeve;
   a chassis connected to the lid, the chassis comprising a hollow cylinder that supports the lid and a hose connector;
   a plunger mechanism connected to the chassis adapted to control a longitudinal displacement of the rotation screw drill along a rotation axis; and
   a suction system connected to the hose connector of the chassis;
   wherein the rotational screw drill is configured to move retractably backward and forward along a longitudinal axis of the sleeve.

2. The device for fracturing and removing ocular lenses according to claim 1, wherein the device is directly and mechanically connected to probes, which provide power, irrigation of a balanced salt solution and hydraulic suction, and a control system controlling the power, irrigation and hydraulic suction.

3. A hand-piece attached to the device for fracturing and removing lens according to claim 1.

4. The hand-piece according to claim 3 further comprising an extender shaft and a motor.

5. The hand-piece according to claim 4, wherein the lid includes a hollow conic section, a hexagonal base, a threaded connector, a plurality of longitudinal blades and stiffener rings, wherein the hollow conic section is a cavity with varying diameters along its length and a distal end of the hollow conic section, has a smaller cavity to rigidly support the sleeve for minimizing vibrations of the extender shaft and allowing fragmented particles to pass therethrough.

6. The hand-piece according to claim 4, wherein the chassis provides support to the lid, the extender shaft, and the plunger.

7. The hand-piece according to claim 4, wherein the chassis contains a vacuum chamber, a triangle-shaped index finger support; a middle finger support, a main cylinder back and sliding rails, wherein the middle finger support has a conical shape, which comprises the hose connector, a thicker threaded wall, and a middle cavity.

8. The hand-piece according to claim 7, wherein the cylinder back supports the extender shaft and includes a bushing to reduce vibrations caused by the rotation of the shaft.

9. The hand-piece according to claim 7, wherein the hand-piece connects a hydraulic system via the hose connector and the probe, wherein the hydraulic system comprises pumps that are driven by a control system, a reservoir and a waste container, wherein the reservoir contains a liquid reserve, feeds balanced salt solution through the pump and the irrigation system to an anterior chamber via an irrigation instrument tip, and wherein the device removes particles and fluid through the hand-piece by the pumps which drag particles towards a waste container through the probe.

10. The hand-piece according to claim 7, wherein the sliding rails are guides in contact with plunger blades.

11. The device for fracturing and removing ocular lenses according to claim 1, wherein the screw has two or more reversed conical propellers.

12. The device for fracturing and removing ocular lenses according to claim 1, wherein the positive angle of the screw tip edge is between 5° and 25°.

13. The device for fracturing and removing ocular lenses according to claim 1, wherein the suction cup (2a) of the sleeve (2) is flexible and collapsible.

14. The device for fracturing and removing ocular lenses according to claim 1, further comprising an irrigation system (30) that is separate and independent from the device.

15. The device for fracturing and removing ocular lenses according to claim 14, wherein the irrigation system (30) comprises a probe (31) and an irrigation instrument tip (30') which irrigates avoiding collapse of the anterior chamber (101) of the eye while performing the scission, grinding and extraction of the lens.

16. A method for fragmentation and removal of the ocular lens, the method comprising the following steps using the device according to claim 1:
    i. irrigating an anterior chamber by means of an irrigation system;
    ii. inserting the sleeve through a 12 meridian incision (second incision);
    iii. capturing or fixing a lens or cataract to the suction cup of the sleeve by activating the suction system through the sleeve;
    iv. irrigating the anterior chamber in a synchronized manner between the suction system and the irrigation system;
    v. fracturing the lens or cataract by drilling the lens with the rotational screw drill;
    vi. breaking a surface and an inner part of the lens or cataract in pieces with a suitable size;
    vii. simultaneously or subsequently vacuuming the lens or cataract pieces; and
    vii. removing the device from the eye.

\* \* \* \* \*